United States Patent [19]

Fischer

[11] Patent Number: 5,328,462
[45] Date of Patent: Jul. 12, 1994

[54] METHODS AND APPARATUS FOR MIXING AND DISPENSING MULTI-PART COMPOSITIONS

[75] Inventor: Dan E. Fischer, Sandy, Utah

[73] Assignee: Ultradent Products, Inc., South Jordan, Utah

[21] Appl. No.: 117,217

[22] Filed: Sep. 3, 1993

[51] Int. Cl.⁵ ............................................. A61M 37/00
[52] U.S. Cl. ...................................... 604/82; 604/191
[58] Field of Search .................. 604/191, 89, 82, 83, 604/87, 88, 91, 411–416; 222/83, 85, 145

[56] References Cited

U.S. PATENT DOCUMENTS

| | | | |
|---|---|---|---|
| 4,392,850 | 7/1983 | Elias et al. | 604/82 |
| 4,871,354 | 10/1989 | Conn et al. | 604/89 |
| 4,979,941 | 12/1990 | Ogle | 604/82 |

*Primary Examiner*—John D. Yasko
*Attorney, Agent, or Firm*—Workman Nydegger & Jensen

[57] ABSTRACT

Methods and apparatus are provided for mixing and dispensing multi-component compositions. The preferred embodiment utilizes a syringe barrel as a mixing chamber and for dispensing of the mixed components. A mixer element, preferable including a paddle member and finger grip means for rotating the paddle member, is provided for insertion into the syringe barrel to effect the desired mixing. A scraper element is used to scrape mixed components from the mixer element so as to retain the mixed components within the syringe barrel upon removal of the paddle member after mixing is completed. Mixing is preferably performed with the multiple components placed in side-by-side orientation within the syringe barrel rather than one on top of another.

20 Claims, 4 Drawing Sheets

METHODS AND APPARATUS FOR MIXING AND DISPENSING MULTI-PART COMPOSITIONS

BACKGROUND OF THE INVENTION

1. Technical Field

The present invention relates to methods and apparatus for use in mixing and dispensing multi-component compositions such as dental cements or impression materials. More particularly, the present invention is directed to syringe mixing and dispensing methods and apparatus.

2. Background Information

Many modern formulations are packaged in two parts, often known as A and B components. Upon mixing, these A and B components typically undergo a chemical reaction which causes the resultant composition to "set up" in some desired manner.

In the dental field, for example, several two-part formulations currently enjoy wide use. Glass ionomer cements and resinous luting cements are frequently used for applications such as securing dental caps in place. Dental impressions are made using A and B components.

In order to work properly, it is important that the A and B components of these two component systems be mixed together rapidly and thoroughly and in the right proportions. Failure to mix rapidly can result in loss of valuable working time with the resultant composition, and can impact the ability to obtain a thorough mix as the composition begins to set up unevenly. Failure to mix thoroughly can result in a composition having less than optimum characteristics. For example, if a poorly mixed composition is used as a cement, it is possible that portions of the cement will fail to reach the chemical strength required for a long-term bond.

Problems of obtaining rapid and uniform mixing are often complicated by differences in the A and B components. Sometimes it is necessary to mix two liquids, while other times it is necessary to mix a powder with a liquid. Sometimes there are equal amounts of the A and B components, but other times there is more of one component than another. Sometimes the two components have similar viscosities, while at other times the two components have widely differing viscosities.

The primary means employed for mixing A and B components has been simple mechanical mixing, such as by means of a mixing bowl or pad and a stir instrument such as a spatula. This method tends to be somewhat messy and time consuming. It is difficult at times to gauge whether the mixing has been sufficiently thorough.

It is also difficult in some instances to prevent formation of small air bubbles in the mixed composition. Most dental compositions are ultimately dispensed from a syringe in order to control the amount dispensed, to permit precise placement of the dental composition, and to prevent premature evaporation of constituents of the composition. This generally requires placement of the mixed compositions into a syringe. Additional air can become entrained during this step. Estrained air bubbles are usually detrimental.

Further, the simple process of mixing the components on a pad or in a bowl and then transferring them to a syringe takes time; this can lessen the available working time to actually utilize the composition. It is not uncommon for so much time to pass during the mixing and syringe-loading steps that the mixed composition becomes effectively unusable.

In order to try and overcome the time delays and the mess inherent in the approach set forth above involving mixing on a pad or in a bowl followed by loading into a syringe, attempts have been made to mix materials directly from a syringe or from a caulking gun. These attempts have involved the use of specially formed tips which effect some mixing as material is dispensed from the syringe or caulking gun. Although useful from the standpoint of minimizing the amount of time used to effect the mixing of A and B components, incomplete mixing is common. Furthermore, the mixing tips utilized are frequently expensive, and hence are usually cleaned for reuse. Such tips are generally difficult to clean and disinfect, making their use burdensome.

SUMMARY OF THE INVENTION

It is a primary object of the present invention to provide improved methods and apparatus for mixing and dispensing multi-component compositions.

Another object of the present invention is to provide improved methods and apparatus for mixing multi-component compositions that substantially prevent the entrainment of air bubbles in the mixed compositions.

Yet another object of the present invention is to provide methods and apparatus for mixing multi-component compositions which effect rapid and thorough mixing.

A further object of the present invention is to provide syringe apparatus and associated methods for mixing multi-component compositions and thereafter dispensing such mixed compositions.

Additional objects and advantages of the invention are set forth hereinbelow in the detailed description, or will be appreciated by the practice of the invention.

To achieve the foregoing objects, and in accordance with the invention as embodied and broadly described herein, the present invention utilizes a syringe barrel as a mixing chamber and for dispensing of the mixed components.

A mixer element, preferable comprised of a paddle member and a finger grip means for rotating the paddle member, is provided for insertion into the syringe barrel to effect the required mixing.

After mixing, the mixer element is removed and a plunger element inserted for use in dispensing material from the syringe barrel in conventional fashion. A scraper element is used to scrape mixed material from the paddle member in order to retain the material within the syringe barrel upon removal of the mixer element.

Mixing is preferably performed with the multiple components placed in side-by-side orientation within the syringe barrel rather than one on top of another.

BRIEF DESCRIPTION OF THE DRAWINGS

In the accompanying drawings, which represent the best mode presently contemplated for carrying out the present invention.

DETAILED DESCRIPTION OF THE PREFERRED EMBODIMENT

The present invention is directed to methods and apparatus for mixing and dispensing multi-component compositions such as dental cements or impression materials. More particularly, the present invention is directed to a syringe mixing and dispensing system useful for rapid and complete mixing of multi-component compositions and subsequent dispensing of the mixed composition.

Figure 1:
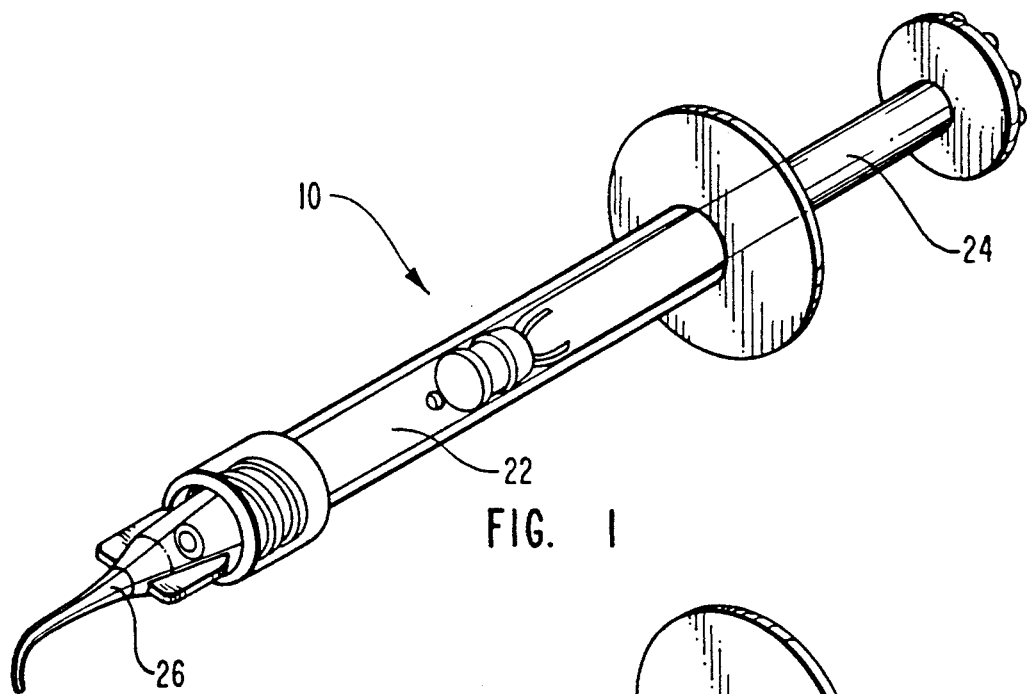
FIG. 1 is a perspective view of a syringe assembly suitable for use in mixing and delivering a multi-part composition.

FIG. 1 illustrates a syringe assembly 10 useful for dispensing compositions, such as dental cements and bonding materials in accordance with the present invention. Syringe assembly 10 includes a syringe barrel 22 fitted with a plunger element 24 of conventional design for delivery of material contained within the syringe barrel through a tip 26. Tip 26 may be of any suitable design for use in particular applications, but is shown as having a structure useful for dispensing dental compositions. Although the remainder of the discussion will be directed to uses of the present invention for mixing and dispensing dental compositions, it should be understood that other materials may be mixed and dispensed using the methods and apparatus disclosed and claimed herein.

Figure 2:
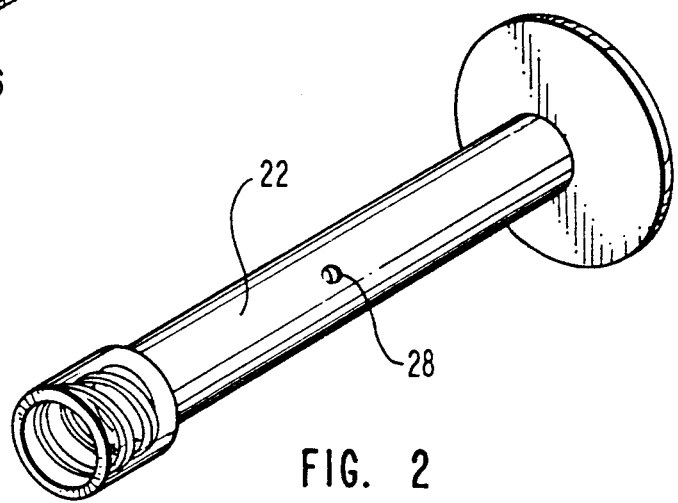
FIG. 2 is a perspective view of the syringe barrel component of the syringe assembly of FIG. 1.

FIG. 2 separately illustrates the syringe barrel 22 of FIG. 1. It is preferred that syringe barrel 22 be provided with a hole 28 for venting air when plunger element 24 is inserted into the syringe barrel after mixing. When material contained within syringe barrel 22 is packed from the discharge end, hole 28 should be located at a position substantially level with the end which will be in contact with plunger element 24. Placing hole 28 higher along the length of syringe barrel 22 will result in retaining air within the syringe barrel, possibly resulting in entrainment of air bubbles during use of syringe assembly 10 to dispense material. Placing hole 28 lower along the length of the syringe barrel will result in leakage of material through the hole upon application of pressure to plunger element 24 to dispense material from syringe assembly 10. Accordingly, it may be desirable to cut hole 28 at the time of use in order to accommodate a particular volume of material desired to be mixed and dispensed, or it may be desirable to provide previously prepared syringe barrels having holes in different locations marked with the optimum volume of material with which it is to be used for mixing and dispensing. It is anticipated that syringe barrels will be provided together with the components of a multi-component composition to be mixed therein and dispensed therefrom, and hence will be provided with a hole 28 located at an optimal location.

An important feature of the present invention is the provision of mixing means for mixing material placed within syringe barrel 22. A presently preferred embodiment of mixing means is mixer element 30 illustrated in FIG. 3. Mixer element 30 includes an elongate paddle member 32 having a length substantially the same as that of syringe barrel 22 with which it will be used. The width of paddle member 32 is preferably about the same as the internal diameter of the syringe barrel so as to effect more complete mixing by scraping material from the wall of the syringe barrel so that it mixes with remaining material contained within the barrel.

Figure 3:
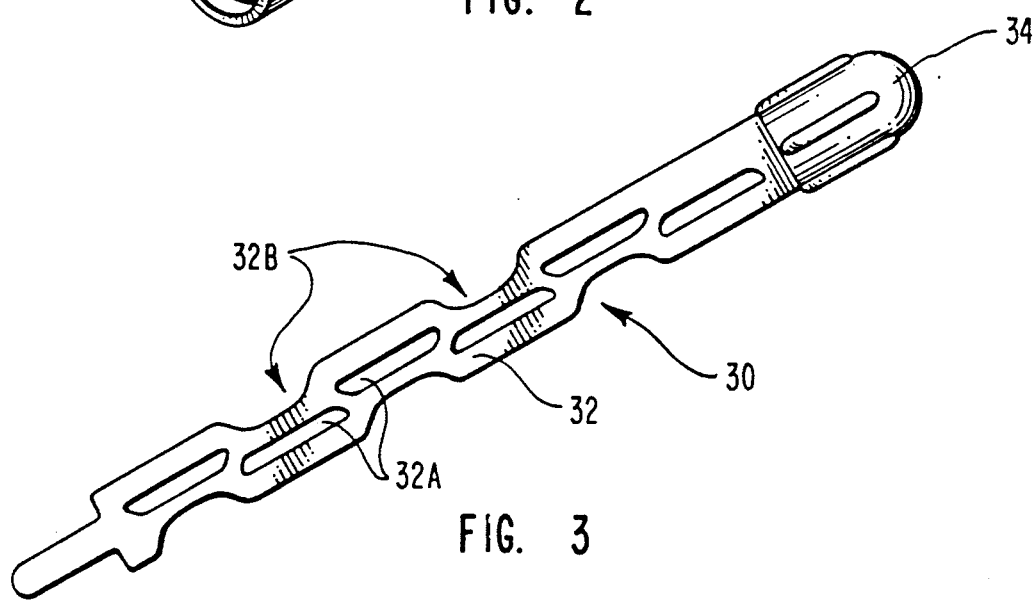
FIG. 3 is an elevation view of a presently preferred embodiment of a mixer element used to effect mixing of multi-part compositions.

Various configurations of paddle members can be used to effect mixing of material contained within the syringe barrel. As illustrated in FIG. 3, it is presently preferred that paddle member 32 be provided with a plurality of generally "D" shaped internal cutouts 32A from the body of the paddle member, and additional generally "D" shaped edge cutouts 32B from the sides thereof. The use of cutouts 32A and 32B assist in generating turbulence as the paddle member is rotated, as discussed below. Although cutouts 32A and 32B are shown along the length of paddle member 32, it should be understood that cutouts are used only in the region where mixing occurs. Hence, if only a small volume is mixed, it may be desirable to provide cutouts only near the end of the paddle member.

Mixer element 30 is also advantageously provided with a finger grip member 34 which serves as means for rotating the paddle member so as to effect mixing of material contained within the syringe barrel.

It is frequently desirable to mix together various components of multi-component compositions, such as some dental cements and bonding materials. For purposes of brevity, the discussion contained herein shall be principally directed to the use of two-component systems, sometimes referred to as A and B component systems. Nevertheless, it should be understood that the methods and apparatus of the present invention will accommodate systems having more than two components.

Figure 4:
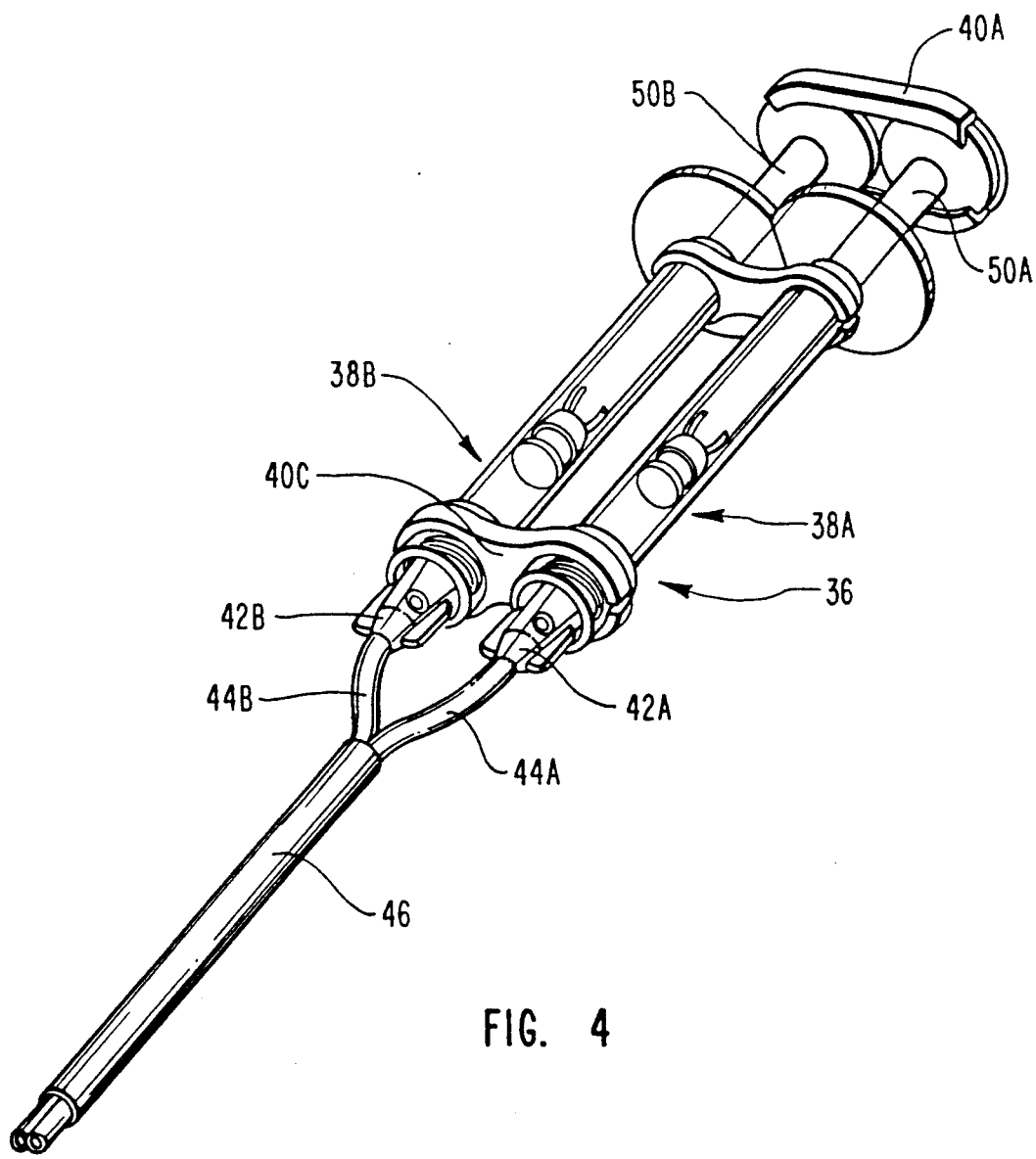
FIG. 4 is a perspective view of a two-syringe device for use in introducing two components of a two-part composition into a syringe barrel such as that shown in FIG. 2 for mixing in accordance with the present invention.

The rotation of mixer element 30 within syringe barrel 22 has been found to be quite effective in mixing A and B components rapidly and completely. It has been determined that the most effective mixing of the A and B components utilizing the apparatus of the invention is accomplished by loading the two components side-by-side within the syringe barrel rather than one on top of the other. Side-by-side loading may be advantageously performed by use of a two-syringe device 36 such as that shown in FIG. 4. FIG. 4 illustrates the use of two syringe barrels 38A and 38B coupled together by clamps 40A, 40B and 40C. The output ends of syringe barrels 38A and 38B are fitted with tips 42A and 42B adapted at one end to secure to the syringe barrel and provided at the other end with tubing members 44A and 44B, respectively. Collar 46 is used to secure tubing members 44A and 44B together, with both tubing members terminating at the same position.

Prior to use, the syringe barrels 38A and 38B of FIG. 4 are filled with A and B components, respectively, of a two-component composition. The output end of syringe barrel 22 is sealed with a cap, such as the cap 48 illustrated in FIG. 7. The output ends of tubing members 44A and 44B are inserted within syringe barrel 22 as far as possible, so that material will be dispensed therefrom near the output end of syringe barrel 22. Then, the two plungers 50A and 50B are simultaneously depressed while slowly withdrawing tubing members 44A and 44B from within syringe barrel 22. This results in placement of material from each of syringe barrels 38A and 38B side-by-side within syringe barrel 22.

It should be understood that additional syringe barrels 38 and associated elements could be added to the device of FIG. 4 in order to accommodate more than two components. Further, the diameters of syringe barrels 38A and 38B could be altered as necessary to effect differing ratios of A and B components. For example, if A and B components are to be added in substantially equal amounts, both syringe barrels 38A and 38B would be substantially identical. If, however, it were desired to add two parts of A to one part of B, syringe barrel 38A should have a cross-sectional area twice that of syringe barrel 38B. It will be appreciated that other modifications could be made in the respective sizes of syringe barrels 38A and 38B to accommodate other mixing ratios. Markings on the sides of syringe barrels 38A and 38B can be used to measure a desired volume to be introduced into syringe barrel 22, or one could look at markings optionally provided on syringe barrel 22 or the location of hole 28 to measure the desired amount of the A and B components.

Figure 7:
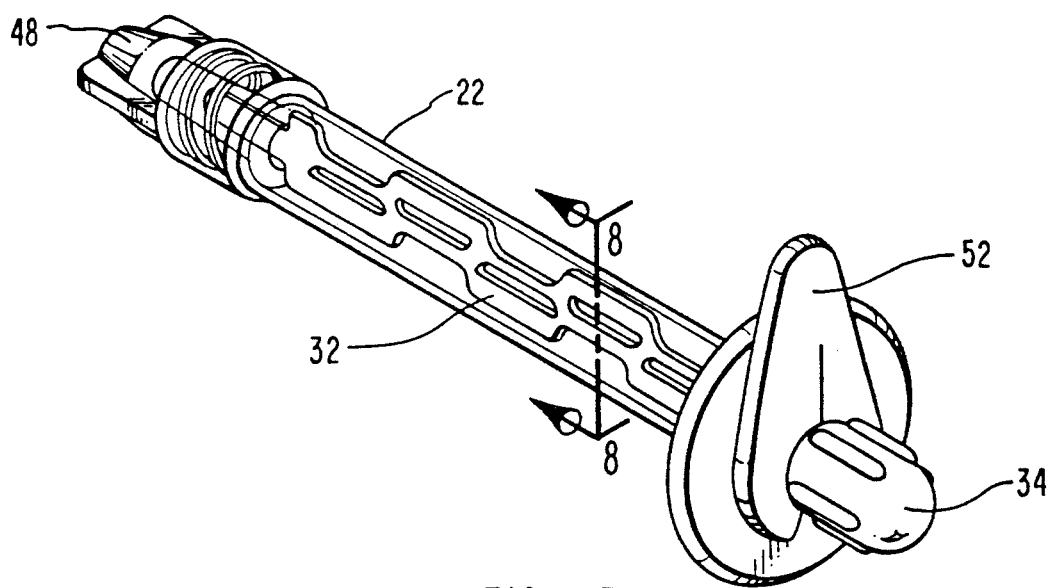
FIG. 7 is a perspective view of the mixer element of FIG. 3 mounted together with the syringe barrel of FIG. 2 and the scraper element of FIGS. 5 and 6.

After the A and B components are loaded in side-by-side fashion within syringe barrel 22 using a method such as that discussed above, mixing is accomplished by inserting mixer element 30 within syringe barrel 22, such as illustrated in FIG. 7.

A feature of the apparatus of the present invention is the provision of scraper means for removing material from the surface of the paddle member of mixer element 30 after mixing is completed. One presently preferred embodiment of suitable scraper means is scraper element 52, illustrated alone in FIGS. 5 and 6, and in combination with other elements of the present invention in FIG. 8.

Figures 5, 6:
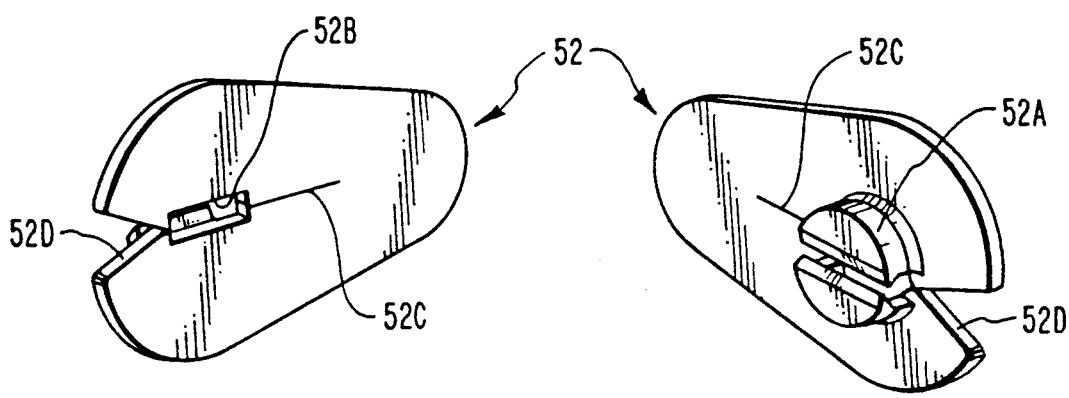
FIG. 5 is a perspective view of one presently preferred embodiment of a scraper element for use with a mixer element following mixing.
FIG. 6 is a perspective view of the reverse side of the scraper element of FIG. 5.

As best seen in FIG. 6, the underside of scraper element 52 is preferably provided with a cylindrical plug member 52A adapted to fit securely within syringe barrel 22. A slot 52B is provided through scraper element, having substantially the same dimensions as the width and thickness of paddle member 32. Prior to use, the paddle member is inserted into slot 52B all the way to the finger grip member, and the combination of the scraper element 52 and mixer element 30 is then secured to syringe barrel 22, as illustrated in FIG. 7. It may be desirable to provide scraper element 52 with a slit 52C and a notch 52D to make easier the task of introducing and removing the paddle member from slot 52B.

Mixing of material contained with syringe barrel 22 is accomplished by rotating mixer element 30. Scraper element 52 will rotate together with the mixer element, making it possible to use the scraper element as the means for rotating the paddle member and to omit the use of separate finger grip member 34.

Figure 8:
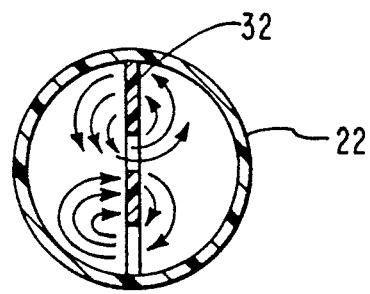
FIG. 8 is a cross-sectional view taken along the lines 8—8 of FIG. 7, showing in schematic form by the use of arrows one manner in which mixing occurs.

The provision of cutouts 32A and 32B generate turbulence as mixer element 30 is rotated; such cutouts function as means for effecting turbulence within the syringe barrel in order to obtain more rapid and complete mixing. Such mixing can be accomplished with little or no entrainment of air bubbles. FIG. 8 illustrates in schematic form the generation of turbulence in response to rotation of paddle member 32. After mixing is complete, mixer element 30 is withdrawn from the syringe barrel while maintaining the scraper element in place. This serves to contain material within syringe barrel 22. After removing the mixer element, the scraper element may be removed and plunger element 24 fitted in place for use in dispensing material from syringe barrel 22. Cap 48 may be removed and replaced with tip 26.

Figure 9:
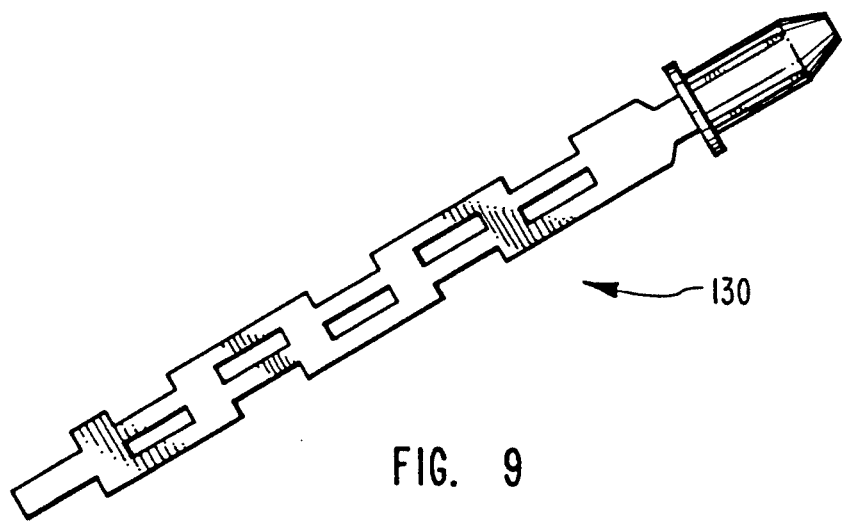
FIG. 9 is an elevation view of an alternative embodiment of a mixer element.

It is to be understood that alternative forms of the elements of the apparatus of the present invention may be made as long as the broad functions set forth above are preserved. For example, FIG. 9 illustrates an alternative embodiment of a mixer element 130. One of ordinary skill will be able to envision many other workable alterations in light of the teachings herein.

Figure 10:
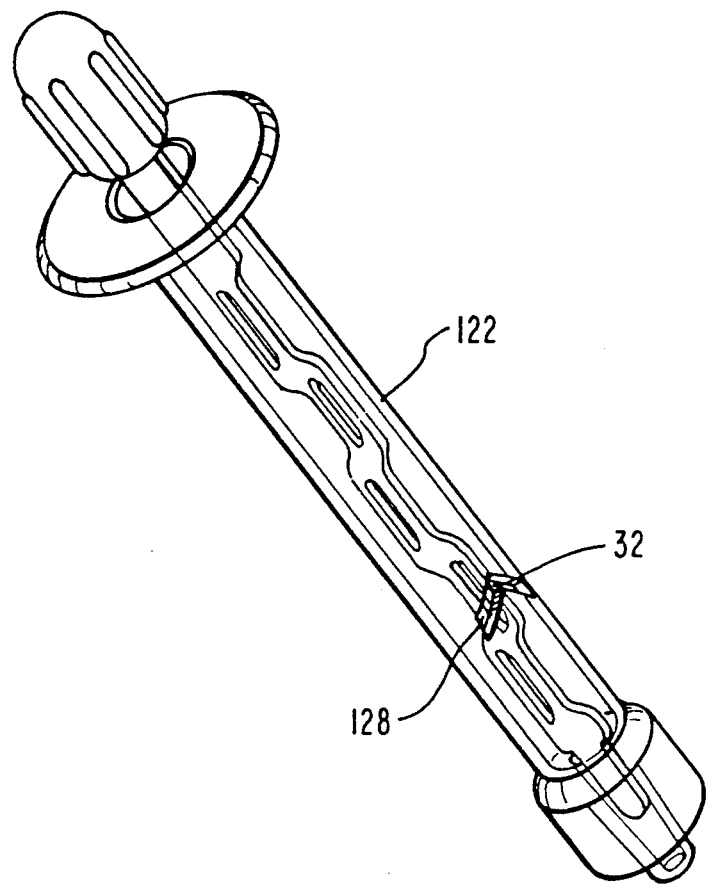
FIG. 10 is a perspective view of a syringe barrel having a chevron shaped hole shown together with the mixer element of FIG. 5.
Figure 11:
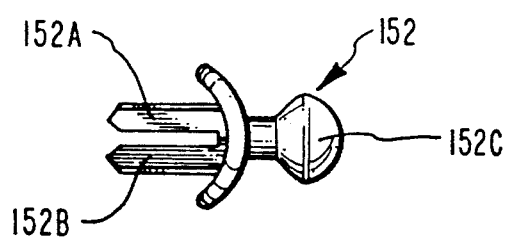
FIG. 11 is a side elevation view of a scraper element suitable for use with the syringe barrel of FIG. 10.
Figure 12:
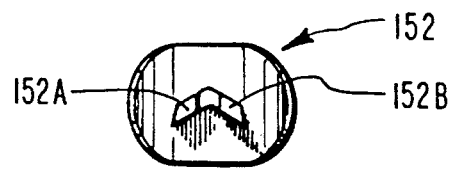
FIG. 12 is an end elevation view of the scraper element of FIG. 11.

Another presently preferred embodiment of the present invention which differs in construction but not function from the discussion set forth above is illustrated in FIGS. 10-12. FIG. 10 illustrates a syringe barrel 122 provided with a generally chevron-shaped hole 128. It is seen that paddle member 30 bisects the center of the chevron. A scraper element 152 (FIGS. 11 and 12) is formed so as to include a pair of projecting fingers 152A and 152B adapted to pass through hole 128 and embrace paddle member 32. A knob 152C is used for grasping scraper element 152 for placement of finger 152A and 152B through hole 128 and later removal of the scraper member. Preferably, the outer ends of fingers 152A and 152B are cut so as to fit snugly against the far wall of syringe barrel 122 when the scraper element is inserted, so that the syringe barrel provides support to the fingers during removal of the mixer element.

Unlike scraper member 52, which is connected to mixer element 30 prior to mixing and rotates together with the mixer element, scraper 152 does not rotate with the mixer element. Accordingly, when using a scraper element of the general type shown in FIGS. 10-12, the scraper element is set aside until after mixing is complete. At that time, the scraper element is inserted through hole 128. The mixer element is then removed, followed by removal of the scraper element and insertion of a plunger element for use in dispensing material from within the syringe barrel.

Once again, it is to be emphasized that other alterations are contemplated within the scope of the present invention. For example, one could use a substantially straight hole in place of the chevron-shaped hole of FIG. 10, together with corresponding changes to the scraper element.

From the foregoing, it may be seen that the present invention provides improved methods and apparatus for mixing and dispensing multi-component compositions. Unlike conventional syringe-mixing systems, the present invention achieves rapid and thorough mixing while substantially preventing the entrainment of air bubbles in the mixed compositions. Further, by achieving the mixing within a syringe barrel, the methods and apparatus of the present invention permit direct and easy dispensing of mixed materials.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by U.S. patent is:

1. A system for mixing and dispensing multi-component compositions, said system comprising;
a syringe barrel for receiving multiple components to be mixed;
mixing means for mixing said components within the syringe barrel, said mixing means including
an elongate paddle member for insertion into said syringe barrel and
means for rotating said paddle member within the syringe barrel so as to effect mixing of components contained therein;
scraper means for removing said components from the surface of the paddle member so as to retain the components within the syringe barrel upon removal of the paddle member after mixing is completed.

2. A system for mixing and dispensing multi-component compositions as defined in claim 1, wherein the paddle means is dimensioned so as to extend in length substantially the whole length of the interior of the syringe barrel and in width substantially across the diameter of the interior of the syringe barrel.

3. A system for mixing and dispensing multi-component compositions as defined in claim 1, wherein the paddle means is provided with means for effecting turbulence in order to assist in mixing components within the syringe barrel.

4. A system for mixing and dispensing multi-component compositions as defined in claim 3, wherein the means for effecting turbulence comprises cutouts in the paddle member.

5. A system for mixing and dispensing multi-component compositions as defined in claim 4, wherein the cutouts in the paddle member are generally "D" shaped.

6. A system for mixing and dispensing multi-component compositions as defined in claim 4, wherein cutouts are provided on the edge of the paddle member and internally of the edge thereof.

7. A system for mixing and dispensing multi-component compositions as defined in claim 1 wherein the scraper means comprises a scraper element having a plug member for placement into the end of the syringe barrel, and a slot for receiving the mixing element.

8. A system for mixing and dispensing multi-component compositions as defined in claim 1, further comprising a hole on the side of the syringe barrel from the interior to the exterior thereof for exhausting air from said syringe barrel upon insertion of a plunger element into said syringe barrel for use in dispensing material contained therein.

9. A system for mixing and dispensing multi-component compositions as defined in claim 8, wherein the hole is elongated, and wherein the scraper means comprises a scraper element having two projecting fingers for insertion through said hole and on opposite sides of the mixing element, thereby serving to scrape material from the mixing element as said mixing element is removed.

10. A system for mixing and dispensing multi-component compositions as defined in claim 1, wherein the means for rotating the paddle member within the syringe barrel comprises a finger grip member secured to the end of the paddle member.

11. A system for mixing and dispensing multi-component compositions, said system comprising;
a syringe barrel for receiving multiple components to be mixed;
mixing means for mixing said components within the syringe barrel, said mixing means including
an elongate paddle member for insertion into said syringe barrel,
said paddle member being provided with means for effecting turbulence in order to assist in mixing components within the syringe barrel, and
means for rotating said paddle member within the syringe barrel so as to effect mixing of components contained therein;
scraper means for removing said components from the surface of the paddle member so as to retain the components within the syringe barrel upon removal of the paddle member after mixing is completed.

12. A system for mixing and dispensing multi-component compositions as defined in claim 11, wherein the means for effecting turbulence comprises cutouts in the paddle member.

13. A system for mixing and dispensing multi-component compositions as defined in claim 12, wherein the cutouts in the paddle member are generally "D" shaped.

14. A system for mixing and dispensing multi-component compositions as defined in claim 12, wherein cutouts are provided on the edge of the paddle member and internally of the edge thereof.

15. A system for mixing and dispensing multi-component compositions as defined in claim 11 wherein the scraper means comprises a scraper element having a plug member for placement into the end of the syringe barrel and a slot for receiving the mixing element.

16. A system for mixing and dispensing multi-component compositions as defined in claim 11, further comprising a hole on the side of the syringe barrel from the interior to the exterior thereof for exhausting air from said syringe barrel upon insertion of a plunger element into said syringe barrel for use in dispensing material contained therein.

17. A system for mixing and dispensing multi-component compositions as defined in claim 16, wherein the hole is elongated, and 18. A system for mixing and dispensing multi-component compositions as defined in claim 11, wherein the means for rotating the paddle member within the syringe barrel comprises a finger grip member secured to the end of the paddle member.

19. A system for mixing and dispensing multi-component compositions, said system comprising;
a syringe barrel for receiving multiple components to be mixed, said syringe barrel being provided with an elongated hole on the side of the syringe barrel extending from the interior to the exterior thereof for exhausting air from said syringe barrel upon insertion of a plunger element into said syringe barrel for use in dispensing material contained therein,
mixing means for mixing said components within the syringe barrel, said mixing means including an elongate paddle member for insertion into said syringe barrel, said paddle member being provided with means for effecting turbulence in order to assist in mixing components within the syringe barrel, and means for rotating said paddle member within the syringe barrel so as to effect mixing of components contained therein;

a scraper element for removing said components from the surface of the paddle member so as to retain the components within the syringe barrel upon removal of the paddle member after mixing is completed, said scraper element having two projecting fingers for insertion through the elongated hole in the syringe barrel and to positions on opposite sides of the mixing element, thereby serving to scrape material from the mixing element as said mixing element is removed.

20. A method for mixing multi-component compositions, comprising the steps of;

placing components to be mixed in side-by-side orientation into a syringe barrel;

placing a paddle element into the syringe barrel;

rotating said paddle element in order to effect mixing of said components; and utilizing scraper means to remove said components from the surface of the paddle member so as to retain the components within the syringe barrel upon removal of the paddle member after mixing is complete.

* * * * *

UNITED STATES PATENT AND TRADEMARK OFFICE
CERTIFICATE OF CORRECTION

PATENT NO. : 5,328,462
DATED : July 12, 1994
INVENTOR(S) : DAN E. FISCHER

It is certified that error appears in the above-indentified patent and that said Letters Patent is hereby corrected as shown below:

Column 1, line 62, "Estrained" should be --Entrained--
Column 2, line 42, "preferable" should be --preferably--
Column 2, line 66, "elevation view" should be --elevational view--
Column 3, line 17, "elevation view" should be --elevational view--
Column 3, line 22, "elevation view" should be --elevational view--
Column 3, line 24, "elevation view" should be --elevational view--
Column 8, line 50, delete ", and" and insert therefor --.--

Signed and Sealed this

Twenty-fourth Day of January, 1995

Attest:

BRUCE LEHMAN

Attesting Officer

Commissioner of Patents and Trademarks